United States Patent [19]

Botta et al.

[11] Patent Number: 4,879,368

[45] Date of Patent: Nov. 7, 1989

[54] OLIGOBENZYLATED HYDROXYCARBOXYLIC ACID DERIVATIVE

[75] Inventors: Artur Botta, Krefeld; Gert Jabs, Odenthal-Gloebusch, both of Fed. Rep. of Germany

[73] Assignee: Bayer Aktiengesellschaft, Leverkusen, Fed. Rep. of Germany

[21] Appl. No.: 104,732

[22] Filed: Oct. 2, 1987

[30] Foreign Application Priority Data

Oct. 17, 1986 [DE] Fed. Rep. of Germany ....... 3635311

[51] Int. Cl.$^4$ ............................................. C08G 61/02
[52] U.S. Cl. .................................. 528/397; 503/210; 524/599; 524/800; 528/206; 528/207; 562/405
[58] Field of Search ........................ 528/397, 206, 207

[56] References Cited

U.S. PATENT DOCUMENTS

| 3,052,640 | 9/1962 | Martin | 528/397 |
| 3,076,785 | 2/1963 | Kiessling et al. | 528/397 |
| 3,657,430 | 4/1972 | Shen et al. | 424/230 |
| 3,924,027 | 12/1975 | Saito et al. | 427/147 |
| 4,046,941 | 9/1977 | Saito et al. | 428/323 |

Primary Examiner—Harold D. Anderson
Attorney, Agent, or Firm—Sprung Horn Kramer & Woods

[57] ABSTRACT

Condensation products of benzyl chlorides and aromatic hydroxycarboxylic acids are suitable for use as color developers in pressure- or heat-sensitive recording materials.

5 Claims, No Drawings

OLIGOBENZYLATED HYDROXYCARBOXYLIC ACID DERIVATIVE

The present invention relates to hydroxycarboxylic acid derivatives and to their use in pressure- or heat-sensitive recording materials.

Condensation products of aromatic hydroxycarboxylic acids and benzyl halides are already known. According to German Reich Patent No. 564,127, they are prepared by heating aromatic hydroxycarboxylic acids together with highly excess amounts of benzyl halides, in general in the presence of small catalytic amounts of anhydrous condensing agents such as $ZnCl_2$ at temperatures of up to over 200°→250° C. They comprise resinous complex mixtures having a low acid value, caused in particular also by the fact that, at the high reaction temperatures, even the hydroxycarboxylic acids used undergo substantial decarboxylation. Since benzyl chlorides are known to undergo a self-condensation to polybenzyl resins in the presence of Lewis acids, the procedure of the abovementioned patent specification leads not only to cocondensation resin but also to a substantial amount of self-condensation resin.

Condensation products of salicylic acid and benzyl cloride which are prepared by the known procedure are dark red brown resins.

Furthermore, German Reich Patent No. 346,384 exposes condensation products of phenols and benzyl halides, which are prepared in the absence of specific condensing agents. However, in the case of phenolcarboxylic acids, such as salicylic acid, which are less reactive than the pure phenols, it is shown in Examples 3 and 5 that the conversion is not complete even if only 2 moles of benzyl chloride are used per mole of salicylic acid.

The condensation materials mentioned are proposed for preparing oil varnishes. Nothing has been disclosed regarding any use for preparing colour developers for pressure and heat-sensitive recording materials. Nor are they suitable for that purpose, owing to the pronounced self-colour.

EP-A-No. 181,283 and JP No. 58-20,779 already disclose metal salicylates and their use as colour developers in recording materials. The preparation of these materials is relatively costly since it is necessary to work in solution. In addition, the substances are obtained in crystalline form and have high melting points. But particularly in the case of pressure-sensitive recording systems, the speed and intensity of colour development depends on how quickly and readily the colour-donating solvent can dissolve the colour developer. Non-crystalline resins having a broad molecular weight distribution and hence a low softening point are of distinct advantage in this respect.

Recording materials for the purposes of the present invention are in particular materials on which visible representations can be produced by imagewise mechanical pressure or by imagewise heating.

These include the known reactive copying papers (cf. M. Cutcho, Capsule Technology and Microencapsulation, Noyes Data Corporation, 1972, pages 242–277; G. Baxter in Microencapsulation, Processes and Applications, edited by J. E. Vandegaer, Plenum Press New York, London, pages 127–143).

Reactive copying papers consist for example of two or more loosely superposed sheets of paper, where in each case the upper sheet contains a donor layer on the reverse side and the lower contains an acceptor layer on the front side. Thus in each case a donor layer and an acceptor layer are in contact with each other. The donor layer contains for example microcapsules whose core material is a solution of a dyestuff former in an organic solvent and the acceptor layer contains a colour developer, i.e. a material which converts the dyestuff former into the dyestuff. A copy is produced when the microcapsules are destroyed by the pressure of a writing implement and the dyestuff former undergoes an imagewise reaction with the colour developer.

If the dyestuff former is embedded not in microcapsules but in a meltable wax, a copy is produced on subjecting the paper to imagewise heating. In this case the system is a thermoreactive recording system.

Dyestuff former and colour developer can also have been applied to the same sheet of paper. This is then referred to as "self contained paper". On such material it is possible to produce for example a script by imagewise pressure or imagewise heating.

Thermoreactive recording systems are preferably used in electronic computers, teleprinters, telex machines and measuring instruments. Markings can also be produced thereon by means of laser beams.

Thermoreactive recording systems can be constructed in such a way that the dyestuff former is dissolved or dispersed in a binder layer and, in a second layer, the colour developer is dissolved or dispersed in the same binder. However, dyestuff former and colour developer can also be dispersed in one layer. The colour developer is softened by heat and comes into contact with the colour donor in the areas where heat is applied. In the course of the coming into contact, the color develops.

Typical examples of known colour developers are active clay substances, such as attapulgus clay, acid clay, bentonite or montmorillonite; and also halloysite, zeolite, silicon dioxide, aluminium oxide, aluminium sulphate, aluminium phosphate, zinc chloride, kaolin and other clays or acidic organic compounds, such as, for example, ring-substituted phenols, salicylic acid, metal salts or salicylic acid esters thereof, and also acidic polymeric materials, such as phenolic polymers, alkylphenol-acetylene resins, maleic acid/colophony resin or partially or completely hydrolysed polymers of maleic anhydride and styrene, ethylene or vinyl methyl ether or polyacetals.

The colour developers can additionally also be used in mixture with inherently unreactive or not very reactive pigments or further auxiliaries such as silica gel. Examples of such pigments are: talcum, titanium dioxide, zinc oxide, chalk; clays such as kaolin and also organic pigments, for example urea-formaldehyde or melamine-formaldehyde condensation products.

Activated clays are moisture-sensitive, i.e. the developed colour can be removed with water or is only very weak in a moist atmosphere. The development of black fluorane dyestuffs, such as, for example, 3-diethylamino-6-methyl-7-anilinofluoran or 3-(N-cyclohexyl-N-methylamino)-6-methyl-7-anilinofluoran, is not possible. On the contrary, corresponding organic colour formers produce reddish black or greenish black images which rapidly pale to become reddish brown.

German Auslegeschrift No. 2,242,250 and Belgian Patent Specification Nos. 784,913 and 802,914 describe metal salts of substituted hydroxyarylcarboxylic acids, for example of salicylic acid, for use as colour developers. DE-A-No. 2,348,639 in addition discloses mixtures of aromatic carboxylic acids or of salts thereof with polymers. The aromatic carboxylic acids and salts thereof are frequently soluble in water, which is why, on applying the aqueous print paste, a portion of the acids diffuses into the interior of the sheet, wherefrom a lower colour-forming capacity and hence a lower color density result.

Phenols for use as colour developers are described for example in U.S. Pat. No. 3,244,550, phenolic resins for example in U.S. Pat. No. 3,672,935 and finally the specific use of bisphenol A resins for exampel in JA Patent Specification No. 063,958.

The known phenols and phenolic resins have in particular the following disadvantages:

The copy exhibits—for example compared with clay developers—a lower intensity or depth of colour.

The rate of development of the copy is low. At the start the copy remains pale until the intensity gradually increases in the course of time.

Coated colour developer papers based on phenolic resin have a pronounced yellowness tendency, which is further strengthened by sunlight and also by artificial light sources.

The preparation of an aqueous phenolic resin dispersion for coating is frequently very difficult, since the resins are very difficult to disperse homogeneously on account of their high melting point, their high melt viscosity and their high tackiness.

In the case of phenol-formaldehyde resins there is the danger of a back formation to phenol and formaldehyde. Formaldehyde is, for known reasons, unsafe.

The invention provides compounds of the following formula I

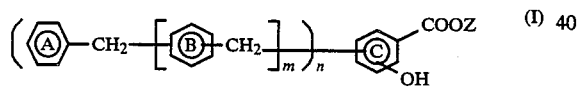

in which
Z denotes hydrogen, alkyl having 1–6 C atoms or $M^{z+}/z$
M denotes z-valent metal cation, in particular of main group II or III or a transition metal cation
z denotes 1 to 4, preferably 2 and 3
n denotes 1 to 4
m denotes 0 to 20, in particular 0–10
subject to the proviso that m+n denotes at least 2, it being possible for the rings A, B and C to be, independently of each other, unsubstituted or substituted, in particular by alkyl, cycloalkyl, aryl, halogen, alkoxy, aryloxy, OH, carboxyl, alkoxycarbonyl or a nitro group and it being possible for the compounds also to be present in bimolecular form where one substituent links 2 radicals of the formula I with each other. In another particularly preferred embodiment, the rings are not substituted.

The invention further provides resins which essentially have compounds of the formula (I). Preferred compounds of the general formula (I) conform to the following formula (II)

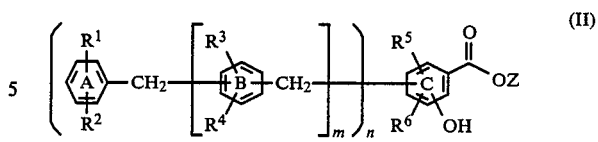

wherein
$R^1$, $R^2$, $R^3$, $R^4$ identically or differently denote hydrogen, alkyl having 1 to 6 C atoms, cycloalkyl, in particular having 5 or 6 C atoms, aralkyl, in particular having 1 to 4 C atoms in the aliphatic part, aryl, in particular phenyl, halogen, alkoxy having 1 to 4 C atoms, phenoxy or nitro,
$R^5$ and $R^6$ identically or differently denote hydrogen, alkyl having 1 to 4 C atoms, cycloalkyl, in particular having 5 to 6 C atoms, aralkyl, in particular having 1 to 4 C atoms in the aliphatic part, aryl, in particular phenyl, halogen, hydroxy, alkoxy having 1 to 4 C atoms, phenoxy, carboxyl, alkoxycarbonyl having 1 to 4 C atoms, nitro,
it being possible for $R^1$ and $R^2$, $R^3$ and $R^4$, $R^5$ and $R^6$ further to represent the members for completing an in particular 6-membered carbocyclic ring together with the benzene nucleus,
or it being possible for in each case one of the radicals $R^1$ to $R^6$ to represent alkylene having 1 to 6 C atoms, alkylidene having 1 to 4 C atoms, phenylene, phenalkylene or phenalkylidene and to link together two radicals of the formula II,
Z denotes hydrogen, alkyl having 1 to 6 C atoms or

M denotes z-valent metal cation of a transition metal or of a metal of main group II or III, in particular such as Zn, Fe, Co, Ni, Cr, Mn, Cu, Mg, Ca, B, Al, Ti, Si, in particular Zn,
m denotes a whole number from 0 to 10,
n denotes a whole number from 1 to 4,
m +n denoting at least 2,
z denotes 1 to 4, in particular preferably 2 or 3.

The invention further provides a process for preparing oligobenzylated aromatic hydroxycraboxylic acids by reacting a hydroxycarboxylic acid with benzyl halides in the presence of an acid catalyst, characterized in that the hydroxycarboxylic acid is introduced first and benzyl halide is gradually added at a rate such that there is always a concentration ratio of aromatic hydroxycarboxylic acid to benzyl halide of ≧1 present, at a temperature at which decarboxylation does not yet take place or at any rate not to any significant extent, in the presence of in particular colour-lightening additives. The reaction can be carried out in the presence of bifunctional or trifunctional branching agents.

The invention further provides compounds obtainable by the process according to the invention.

It has further been found that the oligobenzylated aromatic hydroxycarboxylic acids of the general formula, their esters, preferably their metal salts with transition metals or with metals of main groups II and III of the periodic table of elements, such as Zn, Fe, Co, Ni, Cr, Mn, Cu, Mg, Co, B, Al, Ti, Si, in particular with Zn, are excellent colour developers having high colour intensities in pressure- or heat-sensitive reactive recording systems.

Aromatic hydroxycarboxylic acids which are suitable for use as starting materials are for example salicylic acid, methyl salicylate, ethyl salicylate and butyl salicylate, p-hydroxybenzoic acid, methyl p-hydroxybenzoate, ethyl p-hydroxybenzoate, methylsalicylic acid, tert.-butylsalicylic acid, tert.-octylsalicylic acid, nonylsalicylic acid, methyl-tert.-amylsalicylic acid, cyclohexylsalicylic acid, phenysalicylic acid, chlorosalicylic acid, 2,4-dihydroxybenzoic acid, 3,5-dihydroxybenzoic acid, 1-hydroxynaphthalene-2-carboxylic acid, 3-hydroxynaphthalene-2-carboxylic acid, 4,4'-dihydroxy-diphenylmethane-dicarboxylic acid, 5,5'-penylmethylene-bis-(2-hydroxy-3-methylbenzoic acid), in particular salicylic acid.

Suitable benzyl halides for use as starting materials are for example benzyl chloride, benzyl bromide, o-, m-, p-methylbenzyl chloride, tert.-butylbenzyl chloride, dodecylbenzyl chloride, chlorobenzyl chloride, m-chloro-p-methylbenzyl chloride, chloromethyldiphenyl ether, chloromethyldiphenyl and chloromethylnaphthalene.

The benzyl halides as well as the hydroxybenzoic acids can each be used individually or as mixtures with one another. The amount of benzyl halide which can be condensed in is not limited at the upper end, but in general the colour developer intensity decreases with increasing amount. In general, 2 to 25 moles, preferably about 2 to 7 moles, are used per mole of hydroxybenzoic acid. The branching agents used for preparing bimolecular compounds can also be bifunctional benzyl halides, for example benzyl chloride, benzotrichloride or o-, m-, p-xylylene halides, preferably chlorides. The amounts range in general from 1 to 50%, preferably from 5 to 10%, of the amount of benzyl halide used. The polycondensation proceeds to give a mixture of oligobenzylated hydroxybenzoic acids of random distribution.

Suitable acid catalysts are not only Brönsted acids such as phosphoric acid, sulphuric acid and p-toluenesulphonic acid, but also Lewis acids, such as $AlCl_3$, $BF_3$, $SnCl_4$, $SnCl_2$, $SbCl_5$, $TiCl_4$, $FeCl_3$, $ZnCl_2$, Zn-acetate, Zn-stearate, $CaCl_2$, $MgCl_2$, and even activated argillaceous earths.

The catalyst concentrations can be varied within wide limits. The use of catalytic or stoichiometric amounts of acid depends on whether the oligobenzylated aromatic hydroxycarboxylic acids according to the invention are to be prepared with Z=H or lower alkyl in the form of free acids or esters or with Z=metal in the form of metal salts. In those cases where the free acids or esters thereof are desired, catalytic amounts of Brönsted or Lewis acids, in general 0.01–10%, preferably 0.1–2%, will be used.

In those cases where the metal salt is desired, the condensation reaction is carried out in the presence of stoichiometric amounts of the corresponding metal Lewis acid, in general 1 equivalent being used per mole of hydroxybenzoic acid.

The reaction temperatures depend in each case on the conditions under which there is sufficient elimination of hydrogen halide from the condensation reaction but not as yet any decarboxylation. They are in general between about 50° to 170° C., in particular between about 80° and 130° C.

The reaction is carried out in general in the melt of the reactants. If desired, however, it is also possible to sue solubilizers or to carry out the reaction in a solvent.

Suitable solubilizers are for example: carboxylic acids, such as formic acid, acetic acid, propionic acid, succinic acid, adipic acid. Suitable solvents are for example hydrocarbons, such as carbon tetrachloride, chlorobenzene, dichlorobenzene, trichlorobenzene, trichloroethylene.

For the use according to the invention as colour developers for reactive recording systems it is of vital importance that the resins according to the invention have a satisfactory colour quality. To this end, it is preferable to add to the condensation reaction additives which, according to the invention, surprisingly cause a lightening of the colour. Suitable colour-improving additives are for example reducing agents, such as Zn dust, $SnCl_2$, $TiCl_3$, formaldehyde—if desired in combination with formic acid—or in particular $H_2O$. It has to be regarded as very surprising that the hydrogen halide eliminating condensation reaction according to the invention takes place even in the presence of water and that the formation of markedly brown red byproducts does not occur.

In a general embodiment, the aromatic hydroxycarboxylic acid, optionally in an inert solvent or together with a solubilizer, is heated in the presence of a colour-improving additive, as a rule under a protective gas, such as nitrogen, and in the presence of catalytic or stoichiometric amounts of a strong acid or of a metal salt, optionally together with a substoichiometric amount of benzyl halide, to temperature where the elimination of hydrogen halide starts, and the bulk of the benzyl halide is gradually added at reaction temperature. After the evolution of hydrogen halide has ended, volatile components, such as additives and solvents, are removed in vacuo.

The resin thus prepared can be washed at this stage by adding a solvent and water. Residual traces of acid catalyst have substantially no effect on the colour development properties of the products, so that the wash with water is often superfluous.

In a further embodiment, the condensation is initially carried out in accordance with the catalytic variant, and then the free acid of formula II (Z=H) or its lower alkyl ester (Z=lower alkyl), after hydrolysis with, for example, dilute sodium hydroxide solution, is converted by reaction with the equivalent amount of a metal-donating compound into the desired metal salt (Z=M). The preparation of metal salts of hydroxy acids is known state of the art.

Metal-donating compounds are for example metal hydroxides, oxides, alcoholates or carbonates, metal salts of weak acids, such as acetates or propionates, or metal salts of medium or strong acids in the presence of alkali metal or alkaline earth metal hydroxides, oxides, or carbonates; for example $Zn(OH)_2$, ZnO, Zn-acetate, $ZnCl_2$, $ZnSO_4$, $Zn(NO_3)_2$, $Zn(OC_2H_5)_2$, $ZNCO_3$, $FeBr_3$, $FeCl_3$, $Fe(NO_3)_3.9H_2O$, $Fe_2(SO_4)_3$, Fe-acetate, $AlBr_3$, $AlCl_3$, $Al(OH)_3$, $Al(NO_3)_3.H_2O$, $Al_2(SO_4)_3$, $CoCl_2$, $Co(OH)_2$, $Co(NO_3)_2.6H_2O$, $CoSo_4.7H_2O$, $NiBr_2$, $NiCl_2$, $NiCO_3$, $Ni(OH)_2$, $NiSO_4$, CaO, $Ca(OH)_2$, $CaCl_2$, $Ca(NO_3)_2.4H_2O$, $CaSO_4$, MgO, $Mg(OH)_2$, $MgCO_3$, $MgCl_2$, $Mg(NO_3)_2.6H_2O$, $MgSO_4$, $PbCl_2$, $Pb(NO_3)_2$, $PbSO_4$, $BCl_3$, $BF_3$, $TiCl_3$, $Ti_2(SO_4)_3$, $Ti(SO_4)_2$, $TiOSO_4$, $SnBr_2$, $SnCl_2$, $SnSO_4$, $CuCl_2$, $CuSO_4.5H_2O$, $CrCl_2$, $Cr(NO_3)_3.9H_2O$.

The products according to the invention are preferably almost colourless to pale beige resins having softening points of about 25° to 125° C., and they possess average molecular weights of 300 to 3,000, preferably about 400 to 1,000.

The resins according to the invention can in general be processed into aqueous dispersions by known methods using dispersants. In a particularly suitable process variant, the oligobenzylated hydroxy acids according to the invention of the general formula II in the form of free acids (Z=H) are converted into a aqueous dispersion and reacted in this form with a metal-donating compound to give the corresponding metal salt (Z=metal cation) in the form of a stable aqueous dispersion.

The compounds according to the invention can, if desired in the form of their aqueous dispersions, be used as colour developers, for example for preparing carbon-free copying papers and for preparing thermoreactive recording materials. To this end, the dispersions of the colour developers according to the invention are spread-coated onto a paper carrier web. The formulations of such spread-coating inks is known.

A spread-coating ink to be used for preparing a carbon-free copy paper can be effected for example by mechanical dispersing of the resin powder in water which contains sufficient quantities of dispersant.

Suitable dispersants are for exampel polyvinyl acetates, polyvinyl alcohols, hydroxyethylcellulose, gum arabic, guar gum, locust bean gum or gum ghatti. Particular preference is given to dispersions which, in addition to the colour developers according to the invention, contain combinations of various polysaccharides: gum arabic and guar gum, gum arabic and locust bean gum; evidently the gum arabic acts here as a dispersant, while the other polysaccharide acts as a thickener, preventing resin particles from sedimenting and agglomerating.

Suitable mechanical dispersing means are commercially available colloid mills, bead mills, ball mills and similar homogenizing devices.

To effect further formulation of the spread-coating inks, the aqueous dispersion frequently has added to it absorbents such as chalk, spread-coating clay, aluminium silicates etc.

Furthermore, the compounds according to the invention can be used as "hybrid systems", i.e. they can be combined for example with chemically modified aluminium layer silicates based on montmorillonite.

In addition, the spread-coating inks must be provided with binders to fix the coating material on a carrier. Since paper is the preferred carrier material, these binders are chiefly paper-coating agents, such as gum arabic, polyvinyl alcohol, hydroxymethylcellulose, casein, methylcellulose, dextrose, starch, starch derivatives or polymer latexes. The latter are for example butadiene-styrene copolymers or acrylic monopolymers or copolymers.

In addition to the use in aqueous spread-coating inks, however, incorporation is also possible into printing inks for flexographic or offset printing.

In the preparation of an offset or letterpress printing ink, the developer resins according to the invention can be ground with a suitable varnish on a three-roll mill. The preparation of such offset printing inks is known start of the art.

Flexographic printing inks contain in addition to binders a low-boiling solvent. Suitable solvents for this purpose are for example $C_1$–$C_6$-alcohols, $C_2$–$C_4$-alkanediols, $C_2$–$C_4$-alkanetriols, ethylene glycol monoalkyl ether, aromatic and/or chlorinated hydrocarbons, esters and/or ketones. Solvents also include methanol, ethanol, n-propanol, isopropanol, n-butanol, isobutanol, sec.-butanol, ethylene glycol monomethyl ether, ethylene glycol, 1,2-propanediol, glycerol, acetone, methyl ethyl ketone, toluene, xylene mixtures thereof. The preparation of flexographic printing inks is likewise long-known state of the art.

By means of the printing inks, certain zones of the carrier material can be applied spotwise, for example using offset or flexographic printing equipment.

Using this process it is possible to produce spot-coated developer papers, and the hitherto customary, zonewise neutralizing of a whole-area-coated developer in those areas where for security reasons no copy is to be produced can be dispensed with.

The compounds according to the invention can likewise be used for preparing thermopapers.

Thermoreactive recording systems encompass for example heat-sensitive recording and copying materials and papers. These systems are used for example for recording data, for example in electronic computers, teleprinters, telex machines or in recorders and measuring instruments, such as, for example, electrocardiographs. Image production (marking) can also be effected manually by means of a hot pen. A further way of producing markings by means of heat is laser beams.

The thermoreactive recording material can be constructed such that colour former is dissolved or dispersed in a binder layer and in a second layer the developer according to the invention is dissolved or dispersed in the binder. Another possibility is that both the colour formers and the colour developer according to the invention are dispersed in one layer. The colour developer is softened in specific areas by means of heat and, at the points where heat is applied, the colour former comes into contact with the benzyl resin according to the invention and the desired colour develops immediately.

The preparation of thermopapers is known state of the art. In the preparation and application examples which follow, the percentages indicated, unless otherwise stated, are by weight, and parts are parts by weight.

EXAMPLE 1

1038 g (7.5 mol) of salicylic acid, 1012.8 g (8 mol) of benzyl chloride, 63.2 g (0.5 mol) of $ZnCl_2$ and 50 ml of $H_2O$ are melted in an oil bath with stirring and passing through of nitrogen, and at 120° C. a vigorous elimination of HCl starts. A further 2785.2 g (22 mol) of benzyl chloride are added at 120° to 130° C. in the course of 3 hours, and at the same temperature stirring is continued for a further 5 hours, while nitrogen is being passed through the melt, until the HCl evolution has ended. The subsequent removal of volatile components in vacuo produces only small amounts (about 10 g) of distillate. The yield is 3789 g (99.9% of theory) of a pale yellowish-brownish brittle resin.

OH-number 28; acid number 115

Viscosity: $\pi128°$ C., 102,9 cP, $\pi107°$ C., 374,9 cP, $\pi93°$ C, 1327,6 cP.

The $ZnCl_2$-free substance can easily be isolated by washing the resin with, for example, 1N hydrochlorid acid and then water, otionally with the aid of a solubilizer such as toluene or methylene chlorids.

OH-number 38.5; acid number 108.5.

EXAMPLE 2

By the method of Example 1, the condensation of 553.6 g (4 mol) of salicylic acid with in total 1519.2 g (12 mol) of benzyl chloride in the presence of 21.8 g (0.16 mol) of $ZnCl_2$ and 15 g of $H_2O$ produces 1640 g (99.0% of theory) of a slightly beige brownish highly viscous resin.

EXAMPLE 3

Using the method of Example 1 to condense 553.6 g (4 mol) of salicylic acid with in total 1012.8 g (8 mol) of benzyl chloride in the presence of 21.8 g (0.16 mol) of $ZnCl_2$ and 15 ml of water produces 1284.3 g (99.2%) of a pale yellowish odourless viscous tacky resin.

EXAMPLE 4

A mixture of 34.6 g (0.25 mol) of p-hydroxybenzoic acid, 1.36 g (0.01 mol) of $ZnCl_2$, 63.3 g (0.5 mol) of benzyl chloride and 2 ml of $H_2O$ is carefully melted in an oil bath under nitrogen at 140° to 150° C., then a further 63.3 g (0.5 mol) of benzyl cloride are added dropwise to the melt at 130° to 140° C. in the course of 1½ hours. To complete the elimination of HCl, nitrogen is passed at the same temperature through the melt for a further 5 hours, volatile components (1.5 g) are distilled off in vacuo in the course of about 0.5 hours at about 120° to 140° C. and in this way 119.7 g (96% of theory) of a slightly orange-coloured brittle pulverizable powder having a softening point of 44° to 56° C. are obtained.

EXAMPLE 5

To 304.3 g (2 mol) of methyl salicylate and 0.5 g of Zn-stearate are added dropwise with stirring at 120° C. 1012.8 g (8 mol) of benzyl chloride in the course of 2 hours, during which a vigorous stream of HCl escapes. A temperature of 130° C. is maintained for approximately a further 3 hours by passing dry nitrogen through the melt, and at the end, if appropriate, small amounts (about 7 g) of volatile material are distilled off in vacuo at about 130° C. to obtain in this way 1011.6 g (98.7% of theory) of a brownish beige-coloured viscoous tacky resin.

| Calculated | C 84.35% | H 6.29% | O 9.36% |
|---|---|---|---|
| Found | 84.54% | 6.30% | 9.18% |

EXAMPLE 6

The method of Example 5 is used to otain from 152.0 g (1 mol) of methyl salicylate, 0.25 g of Zn-stearate and 379.8 g (3 mol) of benzyl chloride 411 g (97.3%) of a brownish viscous tacky resin.

| Calculated | C 82.44% | H 6.20% | O 11.36% |
|---|---|---|---|
| Found | 82.60 | 6.13 | 11.20 |

EXAMPLE 7

The method described in Example 5 is used to convert 152.0 g (1 mol) of methyl salicylate, 0.25 g of Zn-stearate and 253.2 g (2 mol) of benzyl chloride to the "dibenzyl" salicylic acid methyl ester. 325 g (97.8%) of brownish transparent viscous oil.

| Calculated | C 79.49% | H 6.07% | O 14.44% |
|---|---|---|---|
| Found | 79.68 | 6.17 | 14.28 |

EXAMPLE 8

152 g (1 mol) of methyl p-hydroxybenzoate, 1 g of Zn-stearate and 126.6 g (1 mol) of benzyl chloride are melted under nitrogen, and a further 379.8 g (3 mol) of benzyl chloride are then added dropwise at 110° to 130° C. in the course of 3 hours. Subsequently HCl elimination is completed by passing dry nitrogen through the melt at about 130° C. for several hours, and if appropriate distilling off residual amounts of volatile material in vacuo at about 150° C. (10 g of oily distillate) to obtain 495 g (96.6% of theory) of a brownish brittle resin.

| Calculated | C 84.35% | H 6.29% | O 9.36% |
|---|---|---|---|
| Found | 84.40 | 6.30 | 9.45% |

EXAMPLE 9

To the resin prepared as described in Example 1 (3789 g, about 7.5 mol) is added, with stirring, as the melt cools down, about 500 ml of toluene at about 80° C., followed by 735 g (about 8 mol) of 45% strength sodium hydroxide solution, and then by a solution of 410.5 g (3.25 mol) of $ZnCl_2$ in 1500 ml of $H_2O$, and stirring is continued thereafter at 80° C. for about 30 min. until 2 clear phases have formed. The aqueous NaCl solution is separated off, and the organic phase is washed once with about 500 ml of $H_2O$ and concentrated. Drying in vacuo at about 100° C. gives a brittle resin having a softening point of 108°–124° C., which is easily grindable to give a pale yellowish beige-coloured powder; the yield is 3975 g.

EXAMPLE 10

To the resin prepared as described in Example 1 (3789 g, about 7.5 mol) is added at about 100° C., as the melt cools down, with fast stirring using a horseshoe stirrer, 1990 g of a 10% strength aqueous solution of a partially hydrolyxed polyvinyl acetate (Moviol ® 8-88 from Hoechst) and 135 g (about 1.5 mol) of 45% strength sodium hydroxide solution, and stirring is continued thereafter at 60°–70° C. for 30 min. until a stable colourless dispersion has formed. A smooth slurry of 265 g (3.25 mol) of ZnO in 1780 g of $H_2O$ is gradually stirred in at such a rate that a temperature of about 40°–45° C. becomes established. That temperature is maintained with vigorous stirring for approximately a further hour until the Zn-complex has formed in full. To remove any specks, the mixture is put through a three-roll mill to give 7955 g of an almost colourless viscous but pourable dispersion.

Viscosity (Brookfield, spindle 7/100 U): 10400 cP.

EXAMPLE 11

To the resin prepared as described in Example 1 (3789 g, about 7.5 mol) are added with stirring after the melt has cooled down, at about 100° C., 3500 ml of xylene, followed by 713.3 g (3.25 mol) of $Zn(Ac)_2 \cdot 2H_2O$, and water and acetic acid are distilled off, initially azeotropically. After further concentrating, at the end in a jet pump vacuum at about 100° C., the "tetrabenzyl"-Zn salicylate is obtained as a brittle pale beige-coloured easily pulverisable resin; the yield is 3973 g, and the softening point is 100°–118° C.

EXAMPLE 12

To the resin prepared as described in Example 1 (3789 g, about 7.5 mol) are added with stirring, after the melt has cooled down, at about 80° C., about 5000 ml of toluene, followed by 100 g of concentrated hydrochloric acid in 1000 ml of water, the aqueous phase is separated off, and the organic phase is washed with about 1000 ml of water. To the Zn-free toluene solution are then added 219 g (3.75 mol) of Mg(OH)$_2$, which is followed by stirring at 80° C. for about 30 min. to form 2 clear phases, distilling off water azeotropically via a separator, filtering the toluene solution and further concentrating, at the end in vacuo at about 100° C. Grinding of the pale brittle resin on a pulverizing mill gives 3812 g of a slightly cream-coloured powder having a softening point of 100°–110° C.

EXAMPLE 13

138.1 g (1 mol) of salicylic acid are melted together with 68.2 g (0.5 mol) of ZnCl$_2$ and 60 ml of acetic acid with stirring under nitrogen. At about 100° C. first 1 g of paraformaldehyde and then 60 ml of formic acid are added, followed at 100°–115° C. by 569.7 g (4.5 mol) of benzyl chloride in the course of 2 h. A temperature of 150° C. is then maintained for 5 hours by passing nitrogen through the melt, small amounts of volatile material are distilled off at the same temperature in vacuo, and 573.2 g (99.6%) of an orange yellowish brittle resin are obtained.

The method of Example 13 was used to react further aromatic hydroxycarboxylic acids with benzyl chloride (see Examples 14–17) and further benzyl chlorides with 1 mol of salicylic acid (see Examples 18–21).

The spread-coating ink was coated by means of an air brush coating range onto a base paper for carbon-free copying papers of 45 g/m$^2$. After drying, the add-on weight was about 5 g/m$^2$ of paper.

If a commercially available CB sheet (for example Autocopy from Zanders) is placed on the coated side of the developer sheet thus obtained and the top sheet is written on, this produces on the developer sheet a deeply coloured copy which fades very little even under the prolonged action of light and not at all under the action of moisture.

EXAMPLE 23

Application Example (Thermopaper)

32 g of the resin of Example 9, 3.8 g of the distearylamide of ethylenediamine, 89 g of kaolin, 20 g of an 88% hydrolysed polyvinyl alcohol and 55 ml of water are ball-milled until the particle size is about 5 μm. In a second ball mill, 6 g of crystal violet lactone, 3 g of an 88% hydrolysed polyvinyl alcohol and 60 ml of water are milled to a particle size of about 3 μm. The two dispersions are added together and coated onto paper in a dry add-on weight of 5.5 g/m$^2$. Heating the paper to 120° C. produces a deep blue colour which has good light and sublimation fastness.

EXAMPLE 24

Application Example 250 parts of resin of Example 13 are ball-milled together with 50 parts of partially hydrolysed polyvinyl acetate (Moviol ® 8-88 from Hoechst) and 200 parts of water until a finely divided (about 5 μm) dispersion containing 50% resin was obtained.

The dispersion was processed into a spread-coating composition and applied to a base paper.

| Example | Starting acid | Benzyl chloride | Resin (Zn-salt) |
| --- | --- | --- | --- |
| 14 | 188 g (1 mol) of 1-hydroxy-naphthalene-2-carboxylic acid | 633 g (5 mol) | 666.1 g (99.4%) brownish beige, brittle |
| 15 | 194 g (1 mol) 5-tert.-butyl-salicylic acid | 379.8 g (3 mol) | 494.4 g (99.7%) orange beige, brittle |
| 16 | 152 g (1 mol) 3-methyl-salicylic acid | 759.6 g (6 mol) | 715.5 g (98.8%) cream-coloured, brittle |
| 17 | 144 g (0.5 mol) 4,4'-di-hydroxydiphenylmethane-3,3'-dicarboxylic acid | 379.8 g (3 mol) | 438.9 g (98.4%) brownish beige, brittle |

| Example | Substituted benzyl chloride | Resin (Zn-salt) |
| --- | --- | --- |
| 18 | 644 g (4 mol) p-chlorobenzyl chloride | 681 g (99.3%) pale beige, brittle |
| 19 | 844 g (6 mol) p-methylbenzyl chloride | 787 g (99%) pale brownish, brittle |
| 20 | 883.5 g (5 mol) 1-chloromethylnaphthalene | 853.6 g (98%) yellowish beige, brittle |
| 21 | 506.4 g (4 mol) benzyl chloride + 70 g (0.4 mol) p-xylylene chloride | 588.8 g (96.9%) orange yellowish, brittle |

EXAMPLE 22

Application Example

(carbon-free copying papers)

3.1 l of water are brought to pH 9.0 with sodium hydroxide solution and 1 kg of China Clay SPS is stirred in. 500 g of a 50% strength resin emulsion prepared as described in Example 10 are added with further stirring. This was followed by the addition of 200 g of a 5% strength aqueous CMC solution and of 160 g of a 50% strength SBR latex binder.

If a commercially available CB sheet (for example Autocopy from Zanders) is placed on the coated side and the top sheet is written on, a deeply coloured copy which is stable to moisture is obtained.

EXAMPLE 25

The resin of Example 12 is processed to give a carbon-free copying paper by the method described in Example 24.

A similar result is obtained.

We claim:

1. An oligobenzylated aromatic acid of the following formula I

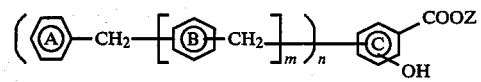

in which
Z denotes hydrogen, alkyl having 1 to 6 C atoms or $$\begin{array}{c} M \\ Z \end{array}$$

M denotes metal cation
z denotes 1 to 4,
n denotes 1 to 4,
m denotes 0 to 20 subject to the proviso that
m+n denotes at least 2, rings A, B and C are unsubstituted or substituted independently of each other or the ologobenzylated aromatic acid can be in bimolecular form wherein 2 radicals of the formula I are linked with each other and wherein the substituents on rings A, B and C represent the members for completing a 6-membered carbocyclic ring with the benzene nucleus.

2. An oligobenzylated aromatic acid according to claim 1, characterized in that M denotes Zn, Fe, Co, Ni, Cr, Mn, Cu, Mg, Ca, B, Al, Ti, Si.

3. An oligobenzylated aromatic acid obtained by reacting aromatic hydroxycarboxylic acids with benzyl halides in the presence of an acid catalyst, characterized in that the hydroxycarboxylic acid is introduced first and benzyl halides are gradually added at a temperature at which no or essentially no decarboxylation occurs.

4. A process for the preparation of an oligobenzylated aromatic hydrocarboxylic acid wherein at least one benzyl halide is gradually added to at least one aromatic hydroxy carboxylic acid in the presence of acid catalyst and in the presence or absence of solvent said addition being at such a rate that the concentration ratio of hydroxy acid to benzyl halide is $\geqq 1$ and wherein reaction temperature is such that no or essentially no decarboxylation occurs.

5. Process according to claim 4, characterized in that a colour-lightening additive is added to the reaction.

* * * * *